United States Patent
Nordberg

(10) Patent No.: US 8,867,810 B2
(45) Date of Patent: Oct. 21, 2014

(54) AUTOMATIC IDENTIFICATION OF DISRUPTIVE EVENTS IN IMAGING SCANS

(75) Inventor: Peter Hugo Glassborow Nordberg, Oxford (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 494 days.

(21) Appl. No.: 13/219,901

(22) Filed: Aug. 29, 2011

(65) Prior Publication Data

US 2012/0051617 A1   Mar. 1, 2012

(30) Foreign Application Priority Data

Aug. 27, 2010 (GB) .................................. 1014331.1

(51) Int. Cl.
*G06K 9/00* (2006.01)
*A61B 6/00* (2006.01)
*G06T 11/00* (2006.01)
*A61B 6/03* (2006.01)

(52) U.S. Cl.
CPC .............. *A61B 6/037* (2013.01); *A61B 6/5205* (2013.01); *A61B 6/5294* (2013.01); *G06T 11/005* (2013.01); *A61B 6/5264* (2013.01)
USPC ....................................................... 382/131

(58) Field of Classification Search
CPC ................... G09B 23/28; A61B 6/032; G06T 2207/10104; G06T 2211/40; G06T 11/005; G06T 7/20
USPC ........................................... 382/100, 128–132
See application file for complete search history.

(56) References Cited

U.S. PATENT DOCUMENTS

| 2004/0223636 A1* | 11/2004 | Edic et al. ..................... 382/131 |
| 2005/0276375 A1 | 12/2005 | Urushiya |
| 2008/0214933 A1* | 9/2008 | Von Busch et al. ........... 600/431 |
| 2009/0003655 A1 | 1/2009 | Wollenweber |

FOREIGN PATENT DOCUMENTS

| JP | 2008258486 A | 10/2008 |
| WO | WO 03/049013 A2 | 12/2003 |

* cited by examiner

*Primary Examiner* — Shefali Goradia
(74) *Attorney, Agent, or Firm* — Schiff Hardin LLP

(57) ABSTRACT

In methods and an apparatus for detecting an incident or behavior in a medical image scan of a subject, a list of image data points captured during the scan is obtained, and a scan period of the scan selected. A model for a distribution of list data over the scan period is obtained, the model at least in part based on the list data from the scan period. List data are compared with the model, by calculating a statistical measure of the self-consistency of the list data with reference to the model.

18 Claims, 7 Drawing Sheets

AUTOMATIC IDENTIFICATION OF DISRUPTIVE EVENTS IN IMAGING SCANS

BACKGROUND OF THE INVENTION

1. Field of the Invention

The present invention is directed to methods and apparatus for detecting incidents or behaviors in a medical image scan of a subject, in certain embodiments to detecting movements of the subject.

2. Description of the Prior Art

In the medical imaging field, several imaging schemes are known. For example PET (Positron Emission Tomography) is a method for imaging a subject in 3D using an injected radioactive substance which is processed in the body, typically resulting in an image indicating one or more biological functions.

Positron Emission Tomography (PET) is becoming an increasingly useful and widespread modality because of its ability to tailor tracers to study specific aspects of physiology and metabolism in vivo. Developments in scanner hardware, reconstruction algorithms and tracers continue to improve the quality of the images; but, as they do so, the effects of motion have become an increasingly important limitation on the overall quality of the information that can be obtained.

The first problem that motion causes is the obvious blurring of the reconstructed image. For 'dynamic' PET, this has implications beyond the loss of spatial detail as it can be hard to tell if the variation in activity (or shape) is due to the movement or from the physiological activity.

The second problem is due to the need to perform attenuation correction during reconstruction. Some of the photons that should be detected will instead be absorbed by other tissues. This process can be compensated for using an attenuation map, a model of the attenuation experienced along different projection directions through the body. This is usually estimated from a CT scan taken immediately before (or after) the PET acquisition on a hybrid scanner. However any motion between the attenuation and emission scans means that the attenuation map is no longer valid and the corrections applied during reconstruction will inevitably introduce artifacts, over- or under-correcting for the attenuation in some regions. This can influence the diagnostic conclusions reached.

The third problem is that iterative reconstruction is non linear, and therefore the image that results from reconstruction of data from a mix of positions is not necessarily a mix of images of the subject in those positions. This point is seemingly ignored in practice, but felt to be significant.

FIG. 1 is a demonstration of the non-linearity of reconstruction, using a basic 2D OSEM algorithm. From left to right: (100) image resulting from reconstruction of a data set comprising of two distinct positions; (102) image resulting from summation of two separately reconstructed images, using the data from each position separately; (104) image resulting from summation of half of two separately reconstructed images, using double the amount of the data from each position separately, such that each reconstruction uses the same amount of data as in the far left case. The bottom row shows histograms of the differences T2-T1 (106); T3-T1 (108) and T3-T2 (110) for points inside the body of the rat.

There are measurable differences in the pattern of noise between the third case and the other two, and the difference between the third and either of the others is significantly greater than between the first two. This indicates that the extra amount of data available to the reconstruction algorithm in the first case relative to the second is not having a significant effect (i.e. producing a smoother image), but the extra data does in the third—where the extra data is self consistent.

Given knowledge of when the subject moved the scan could be split into sections, each corresponding to a single position. There exist ways to register two images together and thus remove the effects of motion, but the detection of when the motion occurred remains a problem.

One example of a disturbance or disruptive even in an imaging scan is a 'twitch': an abrupt motion between otherwise comparatively stable positions, as opposed to a periodic motion like the beating heart (where the practice of gating is widely used).

Twitches have received little attention in the literature; most work on motion has either been centered around registration (where the division of the scan into segments is assumed to have been done somehow) or been in the context of gated motions like breathing or the beating of the heart.

For macro-motions, like twitches, most of the reported approaches involve external optical cameras tracking a target (points that are easily identified, for example infra-red reflector beads) attached to the subject: for example Picard, Y. & Thompson, C. "Motion correction of PET images using multiple acquisition frames" Medical Imaging, IEEE Transactions on, Medical Imaging, IEEE Transactions on, 1997, 16, 137-144. This sort of external monitoring is rarely done in practice; the time required to setup the tracking apparatus imposes too much delay in the clinical workflow and too much stress on patients.

Nehmeh, S. A.; Erdi, Y. E.; Rosenzweig, K. E.; Schoder, H.; Larson, S. M.; Squire, O. D. & Humm, J. L. "Reduction of Respiratory Motion Artifacts in PET Imaging of Lung Cancer by Respiratory Correlated Dynamic PET: Methodology and Comparison with Respiratory Gated PET" J Nucl Med, 2003, 44, 1644-1648 proposes a method that does not need external sensors, rather a radioactive point source attached to the subject is tracked from the PET scanner's data. This reduces, but does not eliminate, the additional workflow. Introducing an extra radiation source, would, however, mean that the additional setup would require proper procedures for handling radioactive materials.

A similar method is suggested in Lu, W. & Mackie, T. R. "Tomographic motion detection and correction directly in sinogram space" Physics in Medicine and Biology, 2002, 47, 1267, but the authors assume that there are sufficiently clear points of high activity within the subject to track and so do not propose the use of an additional, external, point source. This work seems to be only theoretical however.

In short, there is little done to detect twitches in the art: established methods are not seen as being practical for routine use because of the burden entailed.

SUMMARY OF THE INVENTION

An object of the present invention is to address these problems and provide improvements upon the known devices and methods.

In general terms, an embodiment of the method of the invention can provide for detecting an incident or behavior in a medical image scan of a subject, includes obtaining a list of image data points captured during the scan, selecting a scan period of the scan, obtaining a model for a distribution of list data over the scan period, the model being based, at least in part on the list data from the scan period, and comparing list data with the model, wherein the step of comparing includes calculating a statistical measure of the self-consistency of the list data with reference to the model.

This allows a robust way to detect irregularities (such as a twitch), which also uses the raw scan data itself and thus requires no additional setup work.

Suitably, the scan period is a first scan period, and the step of comparing list data with the model includes obtaining list data from a second scan period of the scan.

Preferably, the method includes obtaining a model for distribution of the list data over the second scan period, the model for the second scan period being based at least in part on the list data from the second scan period, wherein the step of calculating the measure of self-consistency includes comparing the model for the first scan period with the model for the second scan period.

This allows the comparison for self-consistency to be made between the models for two scan periods, which provides a straightforward method for this measure. The periods or windows may be adjacent spatially or temporally, or separated (albeit close enough for self-consistency to be measured).

Preferably the step of calculating the measure of self-consistency comprises calculating a joint likelihood using the model or models.

More preferably, the steps of obtaining and comparing comprise systematically obtaining the model or models for each of a sequence of scan periods, and systematically comparing for each current scan period of the sequence.

In one embodiment, the marginal effect of each data point on the measure of self-consistency is computed to perform the systematic comparisons.

Therefore, instead of two scan periods, the method may use a single period, with subsequent updates by data point to generate the series of comparisons. This may be more computationally costly, but provides the advantage of not requiring more than one scan period or window at a time.

Preferably, the method further comprises using the systematic comparisons to generate a time series of self-consistency for the scan.

More preferably, the method further comprises using the measure of self-consistency to determine a feature in the list data relating to the incident or behavior.

Suitably, the feature in the list data is a discontinuity in the time series indicating the time during the scan of a movement of the subject.

In an embodiment, the measure is of local temporal self-consistency of the list data.

Preferably, the medical image scan is a PET scan and the list of image data points is a list of emission events captured in the PET scan.

In other embodiments, the imaging modality may be optical fluorescence tomography, or SPECT.

Suitably, the model is a Poisson distribution model of tracer decay.

Using a Poisson distribution model of the raw data makes modeling of the statistical properties of the image much easier than if the comparison were to be made between reconstructed images, particularly the iterative methods popular for their better image quality.

Preferably, the image data points are image data projection points captured at different times during the scan.

In an embodiment, the method further includes varying a dimension of the scan period or periods in progression of the sequence. Preferably, the dimension is a width of a scan period window.

This allows accuracy of the measure to be maintained even as, for example in PET, the rate of emissions falls later in the scan.

The invention also encompasses a method for detecting an incident or behavior in a medical image scan of a subject, including obtaining a list of image data points captured during the scan, selecting a scan period of the scan, obtaining a model for a distribution of list data over the scan period; comparing list data with the model, wherein the step of comparing includes calculating a statistical measure of the self-consistency of the list data with reference to the model, and using the measure of self-consistency to determine a feature in the list data relating to the incident or behavior.

Suitably, the feature in the list data is a discontinuity in a time series indicating the time during the scan of a movement of the subject.

The invention also encompasses an apparatus for detecting an incident or behavior in a medical image scan of a subject, that includes: a processor configured to obtain a list of image data points captured during the scan, select a scan period of the scan, obtain a model for a distribution of list data over the scan period, the model being based at least in part on the list data from the scan period, and to compare list data with the model, by calculating a statistical measure of the self-consistency of the list data with reference to the model, and to generate an indicator adapted to alert a user to the result of the comparison.

The result may be a status of the measure, or the status in a series of values of the measure, and the indicator may indicate a present status, or an alert for an adverse status.

The invention also encompasses a non-transitory computer-readable storage medium encoded with programming instructions that, when the storage medium is loaded in a computer, cause the computer to execute all methods and all embodiments described above.

The above aspects and embodiments may be combined to provide further aspects and embodiments of the invention.

DESCRIPTION OF THE PREFERRED EMBODIMENTS

Figure 1:
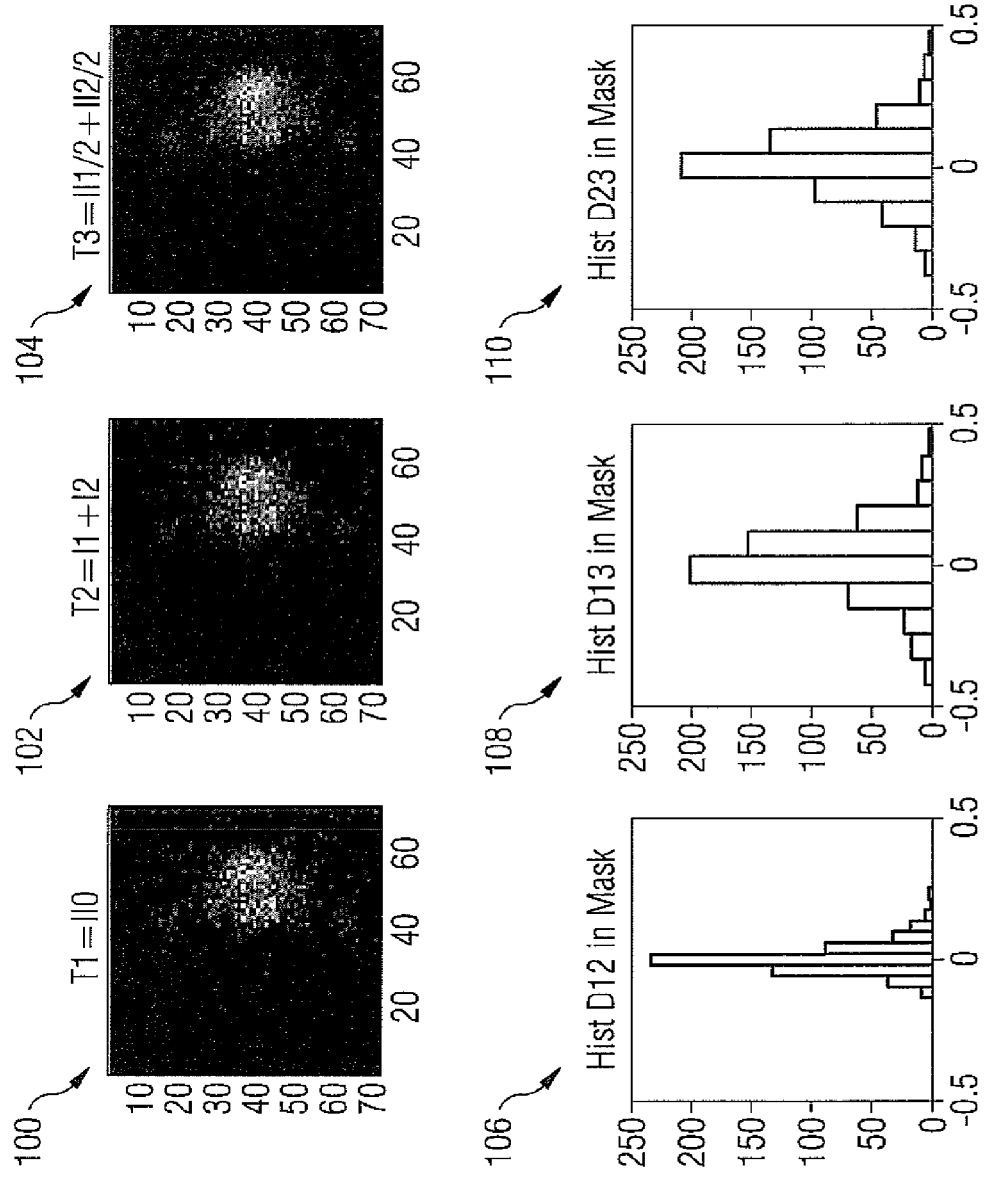
FIG. 1 is a diagram illustrating the non-linearity of reconstruction.

The following terms are used herein, with the following definitions:
PET Positron Emission Tomography
ROI Region of Interest
SUV Standardised Uptake Value Embodiments of this invention focus on 'twitches': abrupt motions between otherwise comparatively stable positions, as opposed to periodic motions like the beating heart (where the practice of gating is widely used: data is combined from different times showing the same phase of the cycle to form composite images).

Although couched in the context of motion the method is driven by the temporal self consistency of the data and, therefore, potentially has applications beyond twitch detection that will be discussed later.

Some principal features of embodiments of the invention are:

Computation of a measure of local self-consistency of the raw PET emission data using some statistical model (and any necessary assumptions) that allows behaviours of interest to be identified as features in the time-series plot of the local self-consistency wherein:

'Local' can be defined in any temporal topology, and restricted to some or all of the scanners field of view 'Behaviours' refers to those of the radio-tracer distribution and may be a consequence of the subject's anatomical motions or physiological action upon the tracer 'Features' referrers to any effect, or combination of effects, on the time-series plot that is predictable given the chosen sense of 'local', the statistical model and assumptions and behaviours of the tracer distribution, and the computation is performed by systematically extracting local subsets of the scan data and calculating the joint likelihood (or surrogate such as log joint likelihood) using the chosen statistical model and assumptions to form the time-series plot of the local self-consistency.

In an embodiment of the invention, the method involves assessing the local self-consistency of the data over time in terms of the statistical properties of the PET data. The radioactive decay of the tracer means that the raw sinogram data is well modelled by a Poisson distribution: the counts for any bin of the sinogram, during a specified interval, can be described as a Poisson variable with a parameter determined by the level of activity along the corresponding line of response. This allows the local likelihood of the data to be estimated for every time during the scan—assuming that there is a constant emission pattern. The intuition is that sudden motions would change the distribution, causing the likelihood to change. Using this statistical measure of local self-consistency the scan can be split into segments that are free from sudden changes.

This Poisson distribution model of the raw data is in contrast to, for example, trying to use reconstructed images, particularly from the iterative methods popular for their better image quality, which makes modelling the statistical properties of the image very difficult.

Using the Poisson-like distributed raw data gives an answer directly related to the physics and processing involved in the emission events and subsequent sinograms from the list data, obtaining a more "real" measurement than would be possible from reconstructed methods. For example, the decay of typical radioactive tracers is Poisson-like. The result is that the correlation with the model is usually so good that any deviation or abnormality is likely to be a detected event, rather than noise or error.

Figure 2:
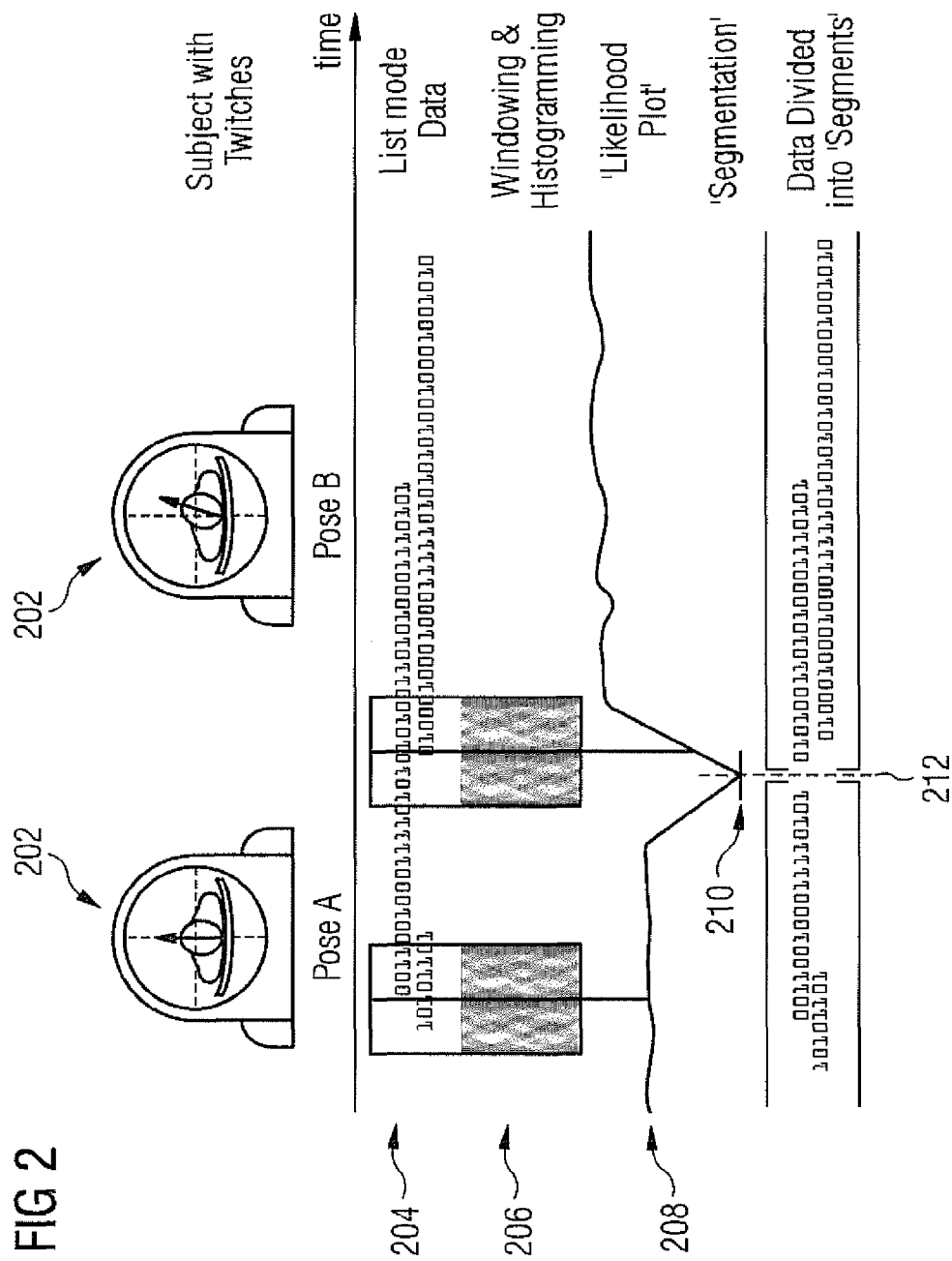
FIG. 2 is a schematic overview of a method according to an embodiment of the invention.

The method of this embodiment can be seen in two aspects: the first is processing the list mode data to generate the 'likelihood plot', the second is to identify the significant features in the likelihood plot corresponding to the twitches and so segment the scan into frames of self-consistent data (each corresponding to a single pose). FIG. 2 provides a schematic overview of a method according to an embodiment, illustrating how for a subject (202) two windows of list mode data (204) are histogrammed into sinograms (206) and their joint likelihood computed (208), with twitches (210) evident as a drop in the likelihood under a hypothesis that there is a common tracer distribution between the two windows. The data can then be divided (212) on this basis.

The first aspect may be more fundamental, the second is a step for using the first to solve the twitch detection problem.

Forming the Likelihood Plot:

For a given point during the scan adjacent 'windows' of data are histogrammed to produce two sinograms. Under a null hypothesis that there is a single emission pattern underlying the data, there should be a single set of Poisson parameters (one for each bin of the sinogram) that fits both the sinograms. For each bin, the parameter that makes the counts observed in the two sinograms most likely is the mean of the two counts; this follows from maximising the joint likelihood expression Bin-wise Joint Likelihood $\qquad$ Equation 1

$$p(s_a^{[\theta,r]} \& s_b^{[\theta,r]}) = \frac{\lambda^{[\theta,r](s_a^{[\theta,r]}+s_b^{[\theta,r]})}e^{-\lambda^{[0,r]}}}{s_a^{[\theta,r]}!s_b^{[\theta,r]}!}$$

$$H0: \lambda^{[0,r]} = \frac{s_a^{[\theta,r]} + s_b^{[\theta,r]}}{2}$$

where $s_a$ represents the counts observed in the sinogram bin at projection angle (theta) and radial offset (r) from the 'after' window; $S_b$ likewise but from the 'before' window. Lambda is the Poisson parameter and H0 the no motion hypothesis.

Given these parameters, the joint likelihood of the two sinograms can be computed on a bin-wise basis. In light of the very small numerical values and large number of sinogram bins it may be difficult to compute the overall joint likelihood of the two sinograms (the product of the bin-wise joint likelihoods) because the value falls below the limits of numerical precision. Instead, the sum of the bin-wise log joint likelihoods is computed. This is monotonically related to the sinogram-wide joint likelihood and therefore serves as a good surrogate.

Sinogram-wise Joint Likelihood $\qquad$ Equation 2

$$p(S_a \& S_b) = \prod_{[\theta,r]} p(s_a^{[\theta,r]} \& s_b^{[\theta,r]})$$

$$\log p(S_a \& S_b) = \sum_{[\theta,r]} \log p(s_a^{[\theta,r]} \& s_b^{[\theta,r]})$$

where $S_a$ and $S_b$ refer to the combined observations of all the elements of the 'after' and 'before' sinograms.

This calculation is repeated for all times during the scan, producing a 'likelihood plot'—strictly 'log-likelihood'—that measures local self-consistency (under the-no-change-in-emission-pattern hypothesis). Near times when the underlying pattern of emissions does change, e.g. because of a motion, the pattern of the counts being recorded in the sinograms will become different from each other, causing the log-joint-likelihood to fall. The scan can then be split into sections based on these local minima. The likelihood plot is influenced by two choices: the length of the windows histogrammed together to form the two sinograms and the temporal resolution, the increment with which the windows are stepped through the duration of the scan.

Appearance of Motion on the Likelihood Plot:

The effect of the two windows rolling past a twitch is the 'V' shaped minimum as would be expected from the assumption of a constant emission pattern not being valid. However, the baseline likelihood in the two poses may not be the same: the re-distribution of counts between different sinogram bins that occurs as a result of the twitch can mean the 'baseline' joint likelihood is different thereafter.

Consider a point source at the centre of the scanner's field of view. All (true) counts will be recorded in one column (radial offset co-ordinate) of the sinogram. Once the point moves off centre the counts will be observed in many columns (although which one depends on the sinogram row—projection angle). The result is that the same number of counts is spread over many bins and so the Poisson distribution for each bin is different, causing the baseline shift.

It follows that the 'V' shape from the two windows rolling past a sudden change is compounded with a progressive change in the baseline level, centred on the twitch time, as more of the new data with its new baseline level is considered by the windows. The relative magnitudes of the baseline change and the minimum control the overall behaviour ranging from a pure 'V' to (almost) perfect slope, with the minimum becoming progressively more asymmetric between the two. Midway between the extremes the minimum disappears: one side of 'V' is completely cancelled by the change in baseline level, this results in a two part slope between the two levels (one part is where one side of the 'V' reduces the slope from the baseline change; the other reinforces the other part). However, the known width of the windows means that there is some prior knowledge of the shape of the 'minimum' that will prove useful in identifying the features of the likelihood plot corresponding to motions in the second half of the method.

Figure 3:
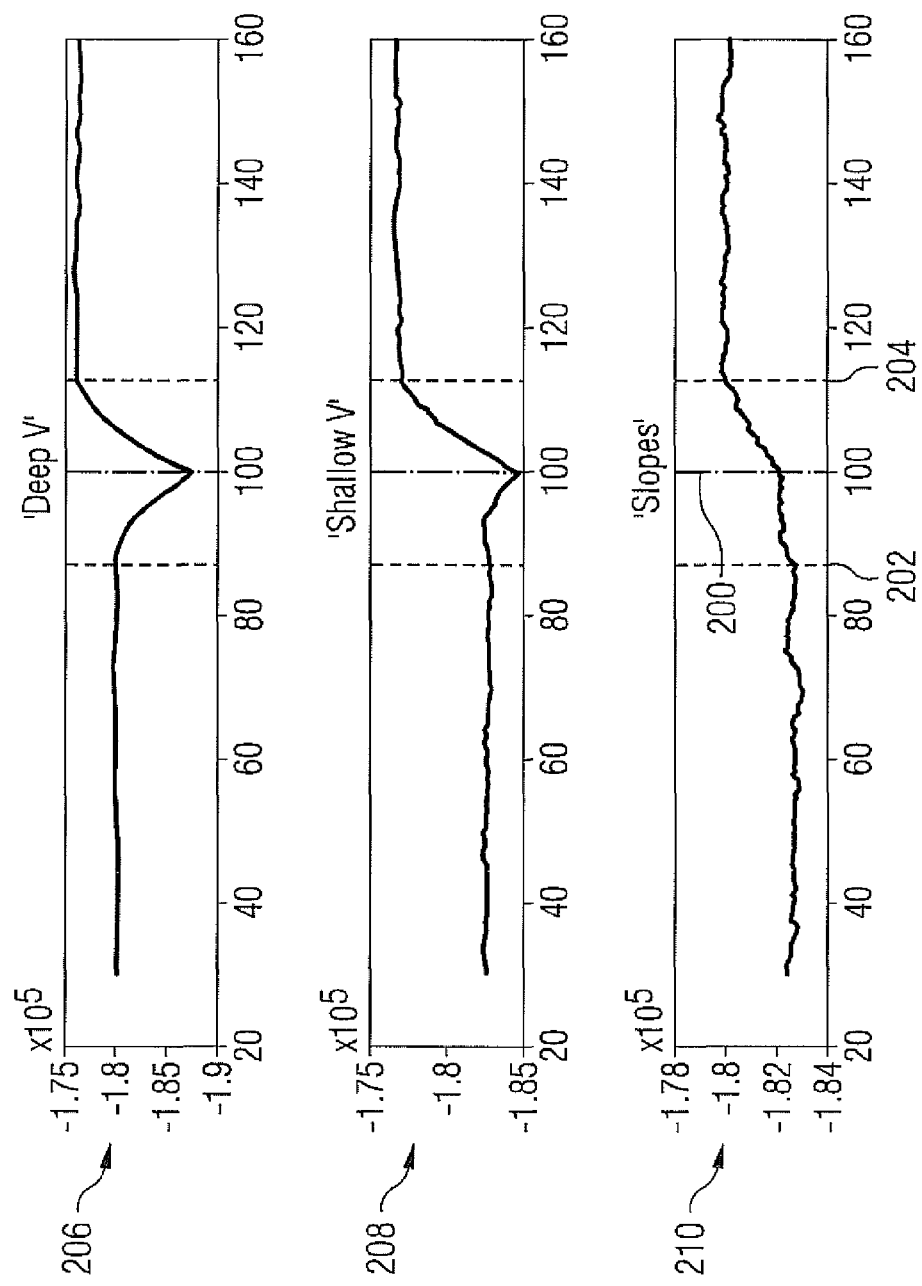
FIG. 3 is a diagram illustrating a measure of variations according to an embodiment of the invention.

FIG. 3 illustrates the variations that occur from the interaction of these two phenomena, the varying results of the interaction of a 'V' shaped minimum and a change in baseline levels. The vertical marks (200) show the twitch time and the extent (202, 204) of the before and after windows around the true twitch time (100s). Examples are given of a deep V (206), shallow V (208), and a slope (210) between two baseline levels.

This example is for an instant change between two perfectly stable positions; real motions will usually exhibit further variations in the 'features' that occur in the likelihood plot from the non-instant motion, other motions (like the beating heart) and tracer kinetics.

Other effects warranting consideration include the corrections normally applied to scanner data such as scatter correction, attenuation correction, detector normalisation, delayed window subtraction (randoms correction). It is usually important to preserve the accuracy of the Poisson model and therefore corrections should not be applied.

Scatter, attenuation and normalisation are not problems themselves—both phenomena can be incorporated into the Poisson model (scatter provides alternative routes from the location of a decay to the detectors, attenuation just means some fraction are not detected, as with the limited sensitivity of the detectors).

Motion causes the scatter pattern to change as well, which will be factored into the calculation of the likelihood plot. With most motions the attenuation will move with the tracer distribution, and so can be ignored in this context—think of the effect of attenuation as a change in the tracer concentration. Motions where this does not hold (e.g. blood flow, or the attenuation from the bed) may still produce a variation in pattern of counts observed.

Variations of detector sensitivity and field of view produce characteristic patterns on the sinogram, e.g. the diagonal grid from the gaps between the rectangular blocks of crystals arranged around the circular bore of the scanner. As these effects are to do with the scanner, not the subject, motion will cause the pattern of counts to change 'behind' them. This will influence the amount of change that a motion has on the overall sinogram. The effect could be positive (consider a small hot region of the sinogram suddenly disappearing behind the diagonal grid) or negative (the parts of the sinogram exhibiting significant variation with motion being obscured by the grid).

Figure 4:
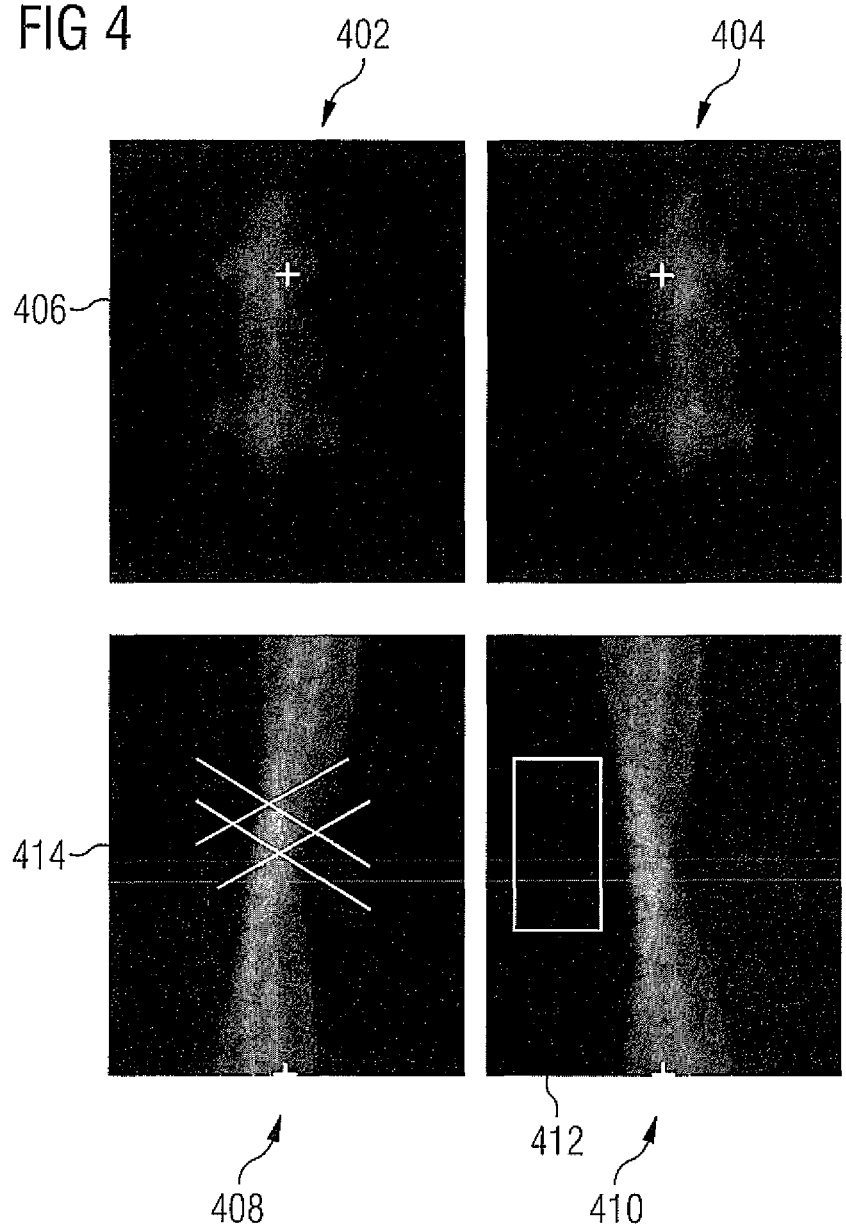
FIG. 4 is a selection of images of motion of a mouse.

FIG. 4 is a selection of images of motion of a mouse. The top row images show coronal projections (402, 404), illustrating displacement and (marker 406) the cross section for which the sinograms in the second row (408, 410) are shown. Note the change in the sinogram due to the motion (other effects like trace kinetics are negligible), scatter (as faint counts in the sinogram outside the main band, e.g. those in the rectangle 412) and the diagonal grid pattern (414) from the crystal block gaps.

The effect of motions on randoms is more difficult to model, but their correction requires subtracting a delayed-coincidence window, and this subtraction certainly appears to violate the Poisson model, so for certain embodiments including randoms is the best course of action.

Decay Correction:

One of the factors that exhibits a strong link to the joint log likelihood computed is the average number of counts in the bins. The overall decay of the tracer during the scan means that the rate of emissions, and therefore observed counts, falls as the scan progresses. This means that, for a fixed window width, the expected number of counts in the windows will fall as the scan progresses. This results in a systematic drift of the likelihood upwards with time. To correct this requires ensuring that there is a constant expected number of counts in the before and after sinograms. This can be achieved by adjusting the widths of the windows based on the time within the scan. Specifically, by lengthening the windows, the number of counts will increase and thus compensate for the falling count rate. If the width of the window is chosen correctly, the net result will be a constant expected number of counts.

For tracers with short half-lives (short relative to the window width) there will also be a need to correct the decay between the before and after windows. The strategy for this correction is exactly the same, the only difference being that the widths of the 'before' and 'after' windows are both chosen adaptively rather than picking a single average width for both windows. Given that it is simple, it makes sense to do both corrections anyway.

Radioactive decay means that the count rate will fall exponentially, so it is easy to choose the window widths for some given time. The window widths are set as some function of the time the expected number of counts in each of the windows can be found by integration. By setting the result of these integrals (one for each window at a given point in time) to be a target number of counts the following equations gives the width of the windows required to achieve that number of counts.

Window Widths in terms of Target Count Number     Equation 3

$$w_b(t) = \frac{1}{\lambda} \ln\left(\frac{\lambda C_*}{N_0} e^{\lambda t} + 1\right)$$

$$w_a(t) = \frac{-1}{\lambda} \ln\left(1 - \frac{\lambda C_*}{N_0} e^{\lambda t}\right)$$

where l is the reciprocal of the half life, C* is the target number of counts, $N_0$ is the initial count rate.

For convenience, one can specify the target number of counts in each window in terms of a duration and the initial count rate. That is to say, instead of choosing N counts per window one can specify a hypothetical window width in seconds which corresponds to having windows of that width, assuming that the count rate were to be constant, matching the average count rate over the duration of the scan. The average count rate can be deduced from the exponential decay behaviour, provided the initial count rate and the duration of the scan are known.

Substituting for the target count number in the expressions for window width gives the two required functions, which conveniently do not need the initial count rate to be measured (the half life is known from the tracer, but the activity depends on the age of the tracer, amount injected, et al.):

Window Widths in terms of an Average 'Timescale'  Equation 4

$$w_b(t) = \frac{1}{\lambda}\ln(W_*(1 - e^{-\lambda T})e^{\lambda t} + 1)$$

$$w_a(t) = \frac{1}{\lambda}\ln(1 - W_*(1 - e^{-\lambda T})e^{\lambda t})$$

where lambda is the reciprocal of the half life, W* is the timescale (window width at average count rate) and T is the overall duration of the scan (the scan from 0 to T defined 'average' count rate).

The decay correction method can be considered as a non-uniform mapping between 'real time' and the temporal space in which the windows of the twitch detection are considered—specifically at the start of the scan less 'real time' is mapped to each unit of 'twitch detector time' than at the end of the scan.

An alternative to dilating windows, as described above, is to decimate the data so as to standardise the count rate throughout the scan. If the above strategy is considered as modifying time to ensure a constant count rate, then this strategy would be considered as changing the data to achieve the equivalent result. This has the obvious disadvantage of requiring data to be discarded from the early sections of the scan in order to reduce the count rate to match the minimum count rate encountered at the end of a scan. This drawback is particularly acute for the early sections of dynamic studies, when the pharmacokinetics of the tracer are fast, and the exact variation is very important to the study. This is also the time when the need to discard data would be greatest.

Dilating the windows has an equivalent sacrifice in that the effective timescale is the increase as the scan progresses.

Segmenting the Scan into Stable Poses:

Segmenting the likelihood plot (and hence the scan) into sections is a more open problem: there are many ways of finding 'features' in time series data and the second-order effects ignored so far (non-instantaneous motion, other smaller motions and tracer kinetics) will require that this second half to the method be investigated in detail when it comes to implementation.

Due to the changes in baseline level a simple threshold will likely not be sufficient. Furthermore, the compounding of the slope between baseline levels and the 'V' shape makes it a particularly difficult type of feature to accurately locate—the interaction will introduce a bias.

For the purposes of demonstrating the benefits of the likelihood plot a two-stage, non-iterative scheme was used. The first stage is based on the local variance that will find either a 'V' shaped minimum or a slope. The second stage interoperates the prior knowledge of the feature (the combined 'V' and slope) to refine the first stage estimate.

Figure 5:
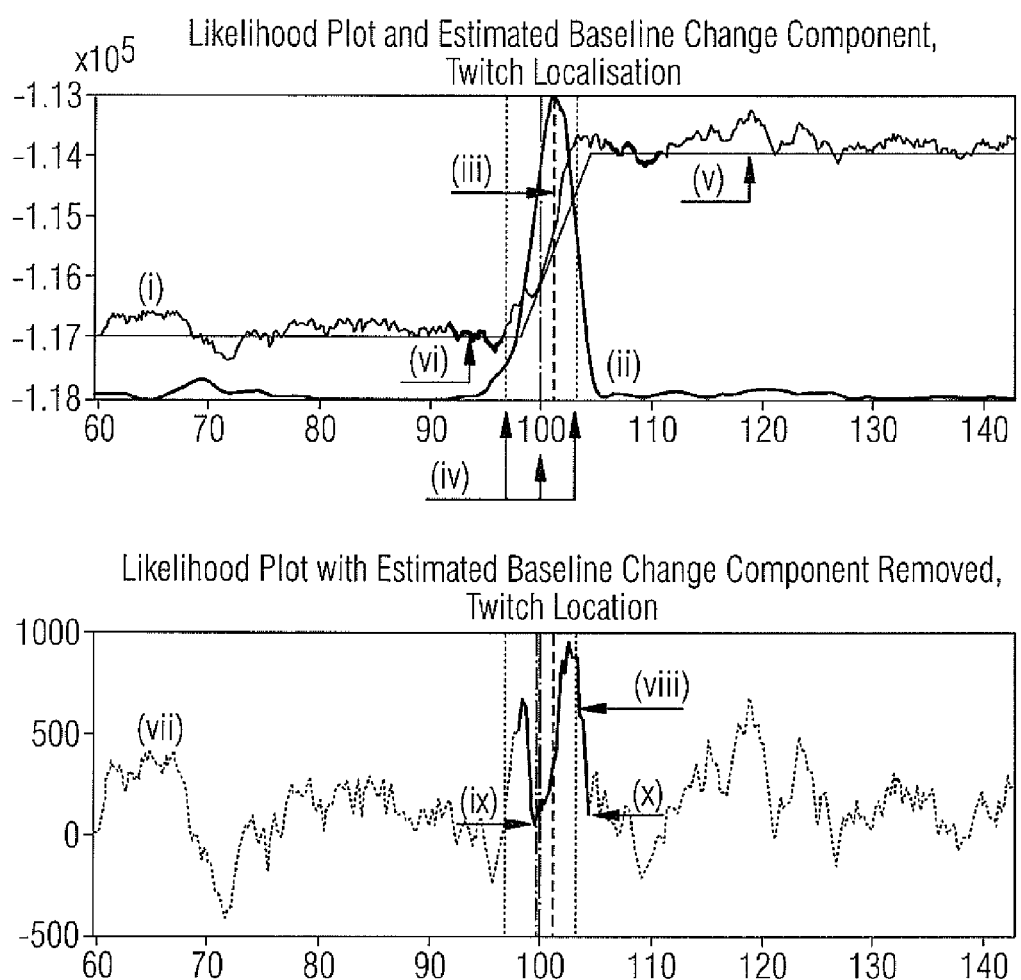
FIG. 5 illustrates the combined two stage segmentation process according to an embodiment of the invention.

FIG. 5 illustrates the combined two stage segmentation process. The top plot shows the likelihood plot (i) and the local variance (ii)—the latter has been scaled to fit on the same axes. The peak of the local variance—and thus the first stage estimate—is marked (iii) along with the true twitch time (100s) and window extents for that time (iv). The baseline component (v) is then estimated from the mean of two regions like (vi), one either side of the first stage estimate. On the bottom plot: the estimated baseline component is removed, leaving (vii) and a minimum sought in the region around the first stage estimate (viii). This minimum is the second stage estimate (ix). Note that the extraneous data (x) could have made the second estimate worse, hence only a minimum on the correct side—the direction of the bias in the first stage is known—of the first estimate would be accepted.

A number of alternatives are available for features of the invention.

Likelihood Plot Formation:

Window Shapes: before and after windows could be defined by any windowing function (in time), not just the rectangular function as used above. This relies on correctly scaling the counts within windows and also extend to asymmetric windows.

Window Configuration: rather than 'before' and 'after' each time point one window could be 'at' the time point and the other fixed at some point, e.g. the start of the scan), or the second window an average one for the some part of the scan's duration, a gap could be introduce between the two windows or there could be some overlap between the windows.

Marginal implementation: instead of there being an implicit histogramming step the marginal effect on the overall likelihood plot could be computed for each coincidence recorded in the list mode file (windowing may not be required at all).

Regional implementation: only coincidence events possibly originating within a chosen region of the scanners field of view are considered.

Tracer Kinetics correction: tracer kinetics known a priori (especially the drop in activity due to the isotope's half life) could be corrected for by scaling the observed counts to different degrees over the course of the scan.

Alternative statistical models: although the Poisson model is felt to be the only correctly justified one, it is possible that a similar plot could be formulated using some alternate model.

Alternative null hypothesis: the assumption that there was no motion could be changed and an alternative likelihood plot formulated in which motions would appear, although as different features.

Hypothesis testing: compare two likelihoods formed using different hypothesise by considering their ratio or some other form of hypothesis test, e.g. a comparison of a no-motion assumption in the choice of the Poisson parameter with the assumption that there was a motion.

Variation of the sinogram resolution: list mode data record the crystal coordinates of the coincidences. There is a conversion from these addresses to sinogram coordinates, as several crystal pairs may count to the same sinogram bin. How this conversion is done depends of the configuration of the sinogram and could be varied—e.g. having fewer bins, and therefore less spatial information, but more counts in each bin. Likewise the setting for maximum ring difference and span during 3D acquisition. Varying the construction of the sinogram would alter the resulting likelihood plot.

Time of flight information: This could be incorporated, for instance, by adding another dimension to the sinogram for bins along each line of response. This would increase the resolution of the sinogram and mean there were fewer counts in each bin. Note that unlike the non-TOF bins, membership of bins in this new time-difference dimension could be considered fuzzy.

Twitch Detection from Likelihood Plot:

Any means of identifying features in the likelihood plot should be considered, along with any pre-processing methods applied to the likelihood plot before the motion features are sought.

Note that real motions, especially non-instant motions, may well not fit the theoretical 'V' plus slope model. In particular, a multi-scale approach to feature identification should be considered.

Figure 6:
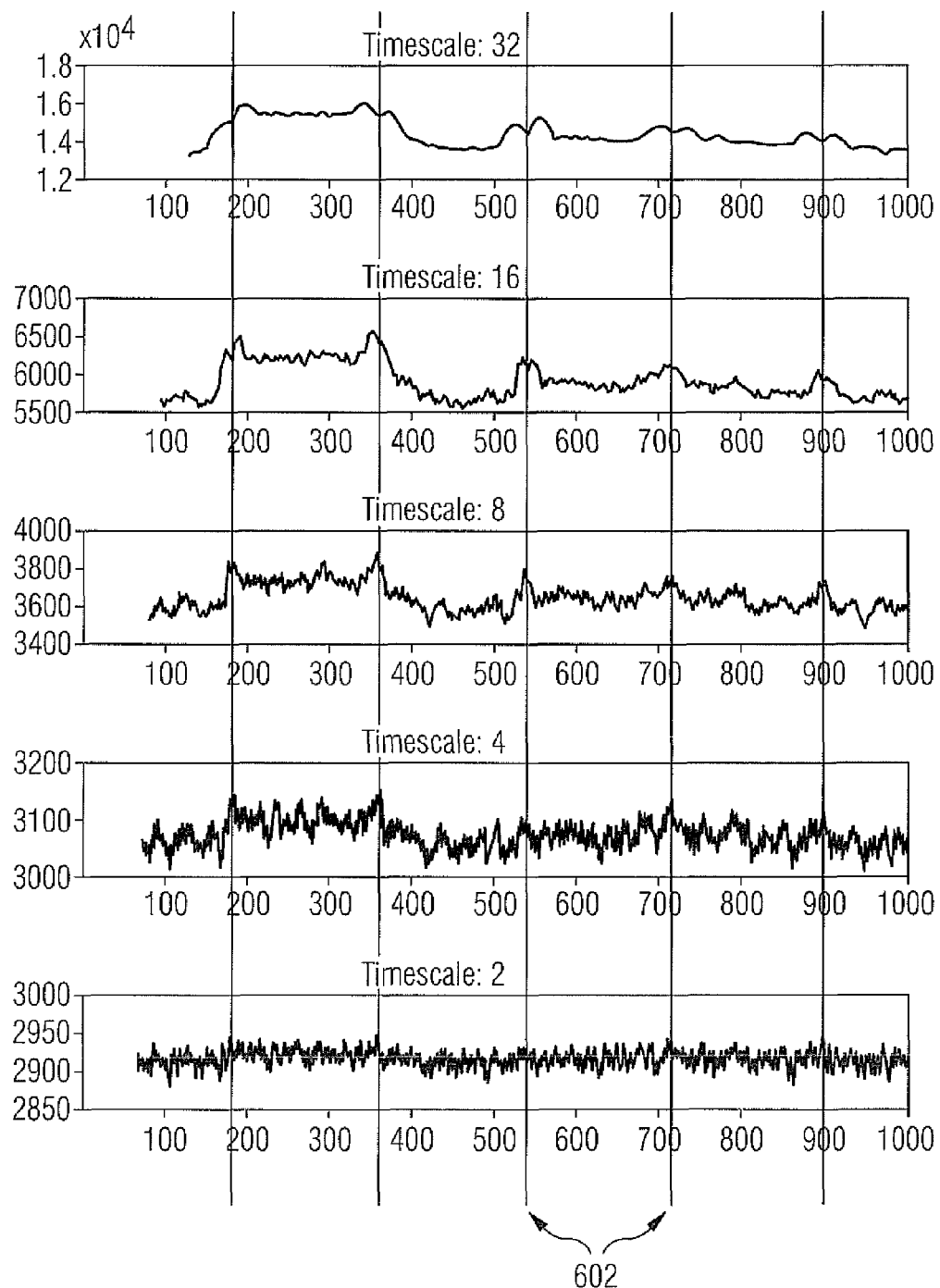
FIG. 6 illustrates a set of likelihood plots generated using a marginal implementation according to an embodiment of the invention.

FIG. 6 illustrates a set of likelihood plots generated using a marginal implementation, with decay correction, at a range of timescales. Note the variety of the features corresponding to motions and the variation with timescale (window width in seconds at average count rate). The vertical lines (602) indicate times that motions were caused.

Alternative Uses of Likelihood Plot:

As the Likelihood Plot is a measure of the local self-consistency of the data (the sense of local being defined by the window configuration) it could be used in several ways other than twitch detection.

Adaptive Framing: dynamic PET scans are often treated as a series of frames, of varying, but predetermined, length. Shorter frames are used at the start of the scan when the tracer kinetics are expected to be fastest. The likelihood plot, as a measure of self consistency, could be used to choose an optimal frame length for any point in the scan.

Intrinsic Gating: periodic motions will have an effect on the data's self consistency, given a suitable timescale (choice of window width and configuration for example), especially in a regional implementation of the likelihood plot. This variation could be detected and potentially used to define gates, just as the ECG (electrocardiogram) signal is for the heart beat or a chest belt is for breathing. Of particular interest would be the ability to gate motion of, say, the diaphragm due to breathing, rather than the breathing itself.

Ad-hoc Gating: By using the correct window configuration (a chosen reference window and a moving test window) the similarity between data in any section of the scan and one or more reference sections could be computed and the data from that section of the scan allocated to that gate. Consider dual-gating (breathing and cardiac cycle): the likelihood that any given window corresponds to the end-diastole/end-expiration phase could be directly estimated.

Re-acquisition of AC data: implementation in real-time would allow on-line detection of twitches and trigger a reacquisition of the attenuation correction scan, or some anatomical scan to allow accurate registration of the two poses. (More relevant to PET-MR, this would allow some diagnostic MR to be acquired simultaneously with the PET, rather than continuously using the MR to track motions.)

Figure 7:
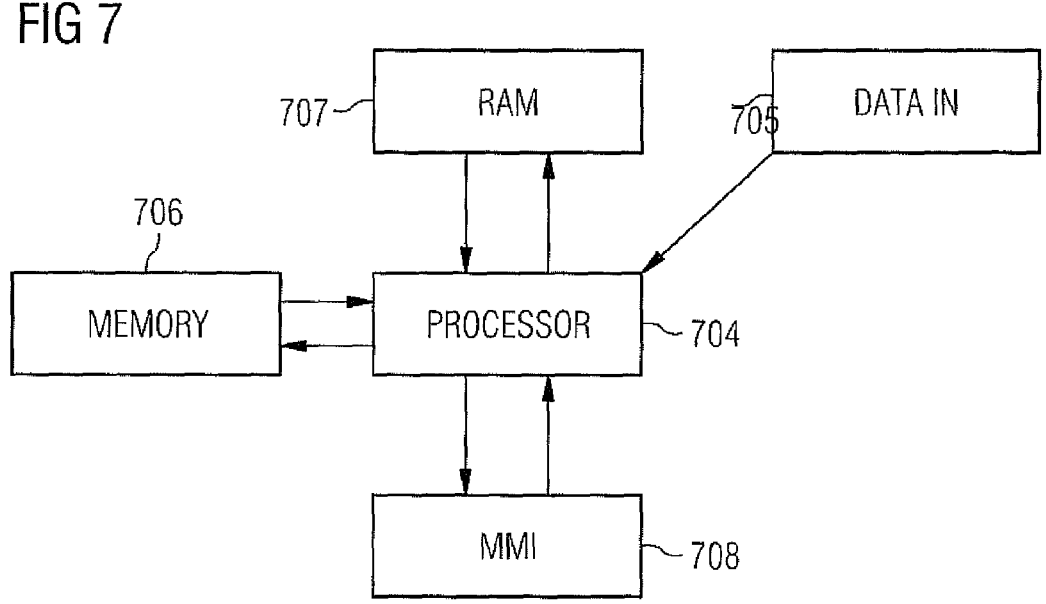
FIG. 7 is a diagram illustrating an apparatus according to an embodiment of the invention.

Referring to FIG. 7, the above embodiments of the invention may be conveniently realized as a computer system suitably programmed with instructions for carrying out the steps of the methods according to the invention.

For example, a central processing unit 704 is able to receive data representative of medical scans via a port 705 which could be a reader for portable data storage media (e.g. CD-ROM); a direct link with apparatus such as a medical scanner (not shown) or a connection to a network. For example, in an embodiment, the processor performs such steps as generating from a first set of the imaging data an intensity projection line along a specified axis of an image volume of the data, converting the projection line to a monogenic signal and extracting phase information from the signal, calculating a function of the phase information to produce processed phase information, and using the processed phase information to organize the feature of interest in the first data set.

Software applications loaded on memory 706 are executed to process the image data in random access memory 707.

A Man-Machine interface 708 typically includes a keyboard/mouse/screen combination (which allows user input such as initiation of applications) and a screen on which the results of executing the applications are displayed.

It will be appreciated by those skilled in the art that the invention has been described by way of example only, and that a variety of alternative approaches may be adopted without departing from the scope of the invention, as defined by the appended claims.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to determine an irregularity in a medical image scan of a subject, comprising:

providing a computerized processor with raw data acquired in a chronological sequence from a subject with multiple detectors, said raw data comprising individually detected photons detected respectively by said multiple detectors, that result from decay of a radioactive tracer administered to the subject;

in said processor, automatically converting said chronological sequence of raw data into list data comprising a chronological listing of respective detections of individual photons by respective detectors among said multiple detectors;

in said processor, selecting a scan period within an overall duration of said medical image scan;

in said processor, automatically determining a model representing a Poisson distribution of decay of said tracer in said list data in said scan period;

in said processor, automatically comparing at least some of said list data to said model by calculating a statistical measure of consistency between said model and said at least some of said list data;

in said processor, automatically determining, from said statistical measure, a time of occurrence of an irregularity in said chronological sequence of list data; and in said processor, emitting an electrical signal designating said time of occurrence of said irregularity in said chronological sequence of said list data.

2. A method according to claim 1, wherein said scan period is a first scan period, and comprising obtaining list data in a second scan period of the medical image scan, and comprising, in said processor, determining a model representing a Poisson distribution of decay of said tracer the list data over the second scan period, and comprising calculating the statistical measure of consistency by comparing the model for the first scan period with the model for the second scan period.

3. A method according to claim 1, wherein the step of calculating the statistical measure of consistency comprises calculating a joint likelihood using the model.

4. A method as claimed in claim 1 wherein said scan period is a first scan period and comprising, in said processor, designating multiple additional scan periods within said overall duration of said medical image scan and comprising systematically comparing the respective list data in said first scan period and the list data in the respective multiple additional scan periods with each other and, for each comparison, calculating said statistical measure of consistency, thereby obtaining a plurality of calculated statistical measures of consistency, and determining said time of occurrence of said irregularity from said plurality of statistical measures of consistency.

5. A method according to claim 4, further comprising varying a dimension of the respective scan periods.

6. A method according to claim 5, wherein the dimension is a width of a scan period window.

7. A method as claimed in claim 4 comprising performing said respective comparisons from a marginal effect of each data point in the respective list data within the respective scan periods being compared.

8. A method according to claim 7, further comprising using the respective comparisons to generate a time series of consistency for the scan.

9. A method according to claim 8, further comprising using the measure of consistency to determine a feature in the list data at said time of occurrence of said irregularity.

10. A method according to claim 9, wherein the feature in the list data is a discontinuity indicating a time during the scan of a movement of the subject.

11. A method as claimed in claim 1 comprising providing said computerized processor with raw data acquired from the subject in a medical image scan selected from the group consisting of a PET scan and an SPECT scan.

12. A method as claimed in claim 1 comprising, in said processor, dividing said list data at least into a first portion of said list data that chronologically precedes said time of occurrence of said irregularity, and a second portion of said list data that chronologically follows said time of occurrence of said list data.

13. A device as claimed in claim 1 wherein said processor is configured to divide said list data at least into a first portion of said list data that chronologically precedes said time of occurrence of said irregularity, and a second portion of said list data that chronologically follows said time of occurrence of said list data.

14. A device to determine an irregularity in a medical image scan of a subject, comprising:

a computerized processor having an input interface that receives with raw data acquired in a chronological sequence from a subject with multiple detectors, said raw data comprising individually detected photons detected respectively by said multiple detectors, that result from decay of a radioactive tracer administered to the subject;

said processor being configured to automatically convert said chronological sequence of raw data into list data comprising a chronological listing of respective detections of individual photons by respective detectors among said multiple detectors;

said processor being configured to select a scan period within an overall duration of said medical image scan;

said processor being configured to automatically determine a model representing a Poisson distribution of decay of said tracer in said list data in said scan period;

said processor being configured to automatically compare at least some of said list data to said model by calculating a statistical measure of consistency between said model and said at least some of said list data;

said processor being configured to automatically determine, from said statistical measure, a time of occurrence of an irregularity in said chronological sequence of list data; and said processor comprising an output interface at which an electrical signal, designating said time of occurrence of said irregularity in said chronological sequence of said list data, is emitted.

15. A device as claimed in claim 14 wherein said raw data acquired from the subject in a medical image scan are raw data selected from the group consisting of PET scan data and SPECT scan data.

16. A non-transitory, computer-readable data storage medium encoded with programming instructions that, when the storage medium is loaded in a computer, cause the computer to:

receive raw data acquired in a chronological sequence from a subject with multiple detectors, said raw data comprising individually detected photons detected respectively by said multiple detectors, that result from decay of a radioactive tracer administered to the subject;

convert said chronological sequence of list data from said chronological sequence of raw data into list data comprising a chronological listing of respective detections of individual photons by respective detectors among said multiple detectors;

select a scan period within an overall duration of said medical image scan;

determine a model representing a Poisson distribution of decay of said tracer in said list data in said scan period;

compare at least some of said list data to said model by calculating a statistical measure of consistency between said model and said at least some of said list data;

determine, from said statistical measure, a time of occurrence of an irregularity in said chronological sequence of list data; and emit an electrical signal designating said time of occurrence of said irregularity in said chronological sequence of said list data.

17. A non-transitory, computer-readable data storage medium as claimed in claim 16 wherein said raw data acquired from the subject in a medical image scan and raw data selected from the group consisting of PET scan data and SPECT scan data.

18. A non-transitory, computer-readable data storage medium as claimed in claim 16 wherein said programming instructions cause said computer to divide said list data at least into a first portion of said list data that chronologically precedes said time of occurrence of said irregularity, and a second portion of said list data that chronologically follows said time of occurrence of said list data.

* * * * *